(12) United States Patent
Brait et al.

(10) Patent No.: US 8,361,353 B2
(45) Date of Patent: Jan. 29, 2013

(54) METHOD FOR MAKING NOVEL COMPOSITIONS CAPABLE OF POST FABRICATION MODIFICATION

(75) Inventors: Axel Brait, San Rafael, CA (US); Shiao H. Chang, Pasadena, CA (US); Patrick Case, Culver City, CA (US)

(73) Assignee: Calhoun Vision, Inc., Pasadena, CA (US)

( * ) Notice: Subject to any disclaimer, the term of this patent is extended or adjusted under 35 U.S.C. 154(b) by 413 days.

(21) Appl. No.: 11/486,615

(22) Filed: Jul. 14, 2006

(65) Prior Publication Data

US 2006/0273479 A1 Dec. 7, 2006

Related U.S. Application Data

(63) Continuation of application No. 10/911,029, filed on Aug. 3, 2004, now abandoned.

(51) Int. Cl.
*B29D 11/00* (2006.01)
*B29C 35/08* (2006.01)

(52) U.S. Cl. .......... 264/1.38; 264/1.7; 264/2.6; 264/2.7; 264/494; 264/344

(58) Field of Classification Search .................. 264/1.1, 264/1.36, 1.38, 1.7, 2.6, 2.7, 232, 340, 344, 264/494, 496
See application file for complete search history.

(56) References Cited

U.S. PATENT DOCUMENTS

| | | | |
|---|---|---|---|
| 4,312,801 A * | 1/1982 | Hiriart Bodin et al. | 524/722 |
| 5,296,305 A | 3/1994 | Baude et al. | |
| 5,684,636 A | 11/1997 | Chow et al. | |
| 5,807,906 A | 9/1998 | Bonvallot et al. | |
| 6,020,409 A * | 2/2000 | Alvarez et al. | 524/267 |
| 6,450,642 B1 | 9/2002 | Jethmalani et al. | |
| 6,846,892 B2 * | 1/2005 | Kindt-Larsen et al. | 526/320 |

FOREIGN PATENT DOCUMENTS

| | | |
|---|---|---|
| CN | 1346251 | 4/2002 |
| EP | 1369710 | 12/2003 |
| WO | WO-00/41650 | 7/2000 |
| WO | WO-03058287 | 7/2003 |

OTHER PUBLICATIONS

Chinese Office Action issued Dec. 5, 2008, issued during the prosecution of Chinese Patent Application No. 200580033208.2.
International Preliminary Report on Patentability issued Feb. 6, 2007, during the prosecution of International Application No. PCT/US2005/027392. Published Feb. 6, 2007.
International Search Report issued Jan. 22, 2006, during the prosecution of International Application No. PCT/US2005/027392. Published Apr. 12, 2007.
Written Opinion issued Jan. 22, 2006, during the prosecution of International Application No. PCT/US2005/027392. Published Feb. 3, 2007.
Supplemental European Search Report issued Aug. 15, 2008, during the prosecution of European Application No. EP 05 77 8372.

* cited by examiner

*Primary Examiner* — Mathieu D. Vargot
(74) *Attorney, Agent, or Firm* — Fulbright & Jaworski L.L.P.

(57) ABSTRACT

The invention relates to a novel method for preparing materials whose properties can be manipulated after fabrication. In this process, a base material is created in a manner that provides spaces or voids which can then be filled with a modifying composition. The method is particularly useful in the manufacture of light adjustable optical elements such as intraocular lenses.

11 Claims, 3 Drawing Sheets

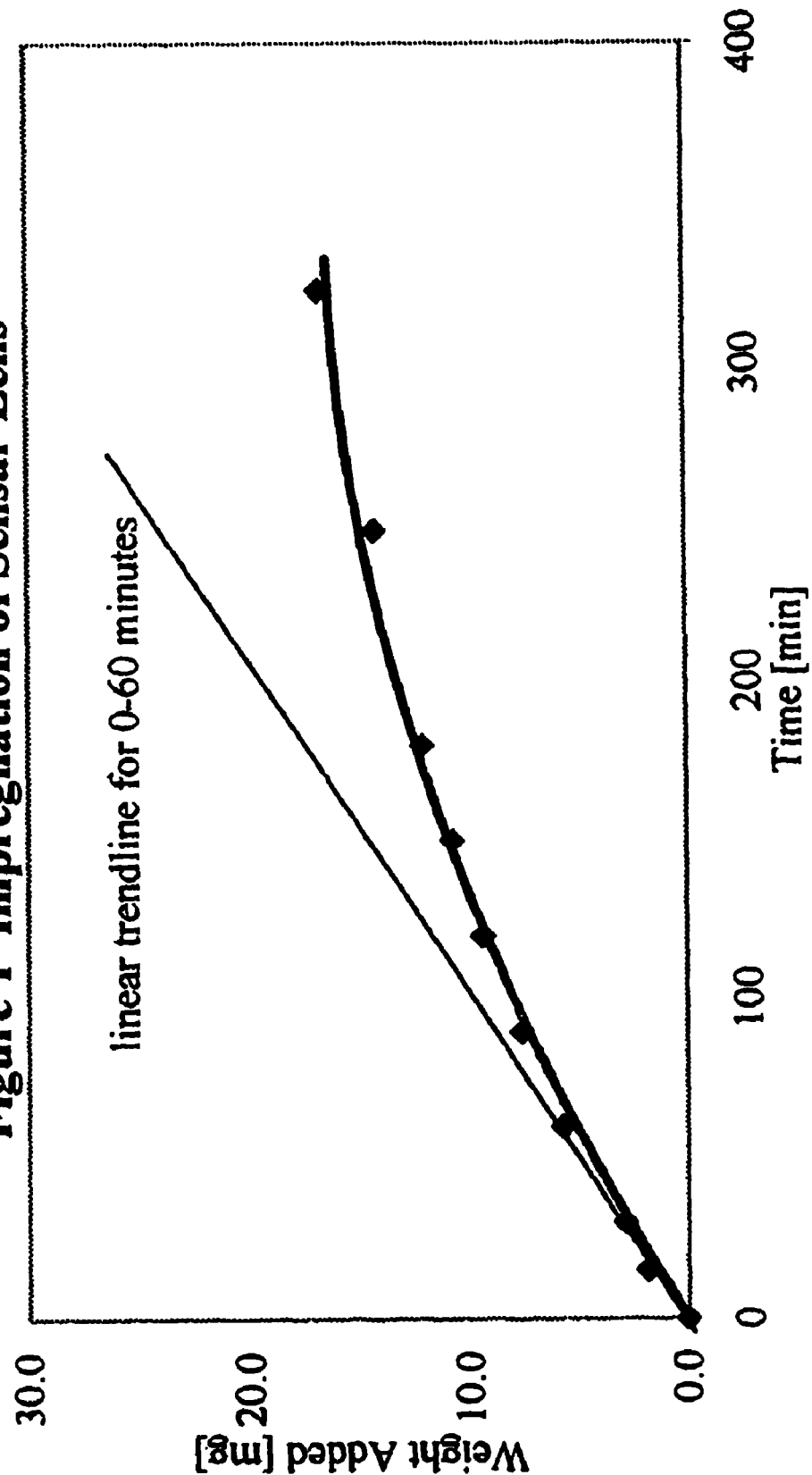
Figure 1 Impregnation of Sensar Lens

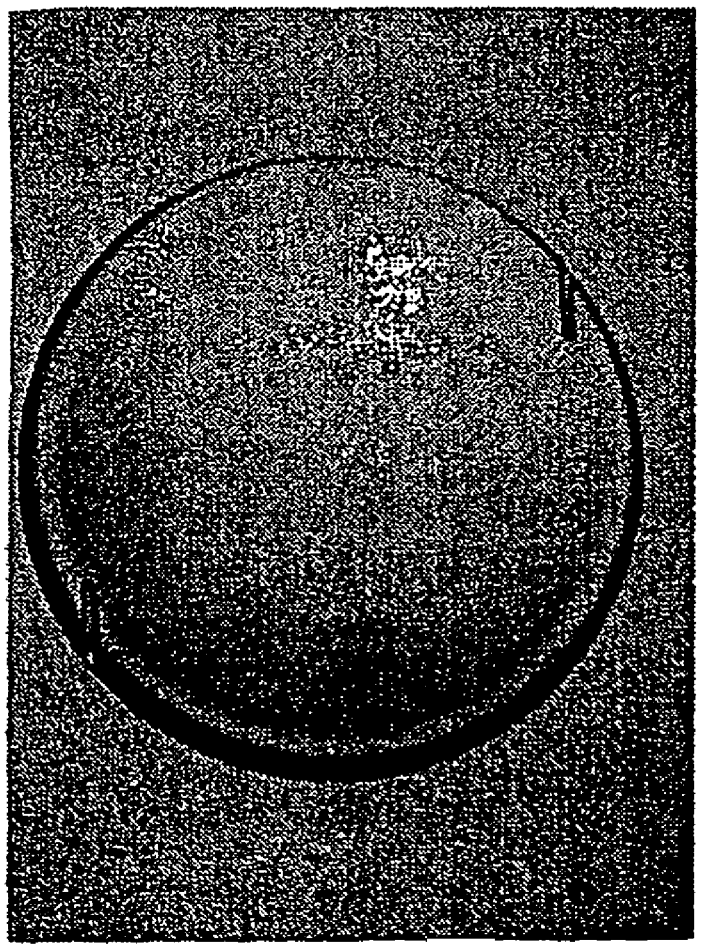
Figure 2 Micrograph of an impregnated acrylic IOL before irradiation

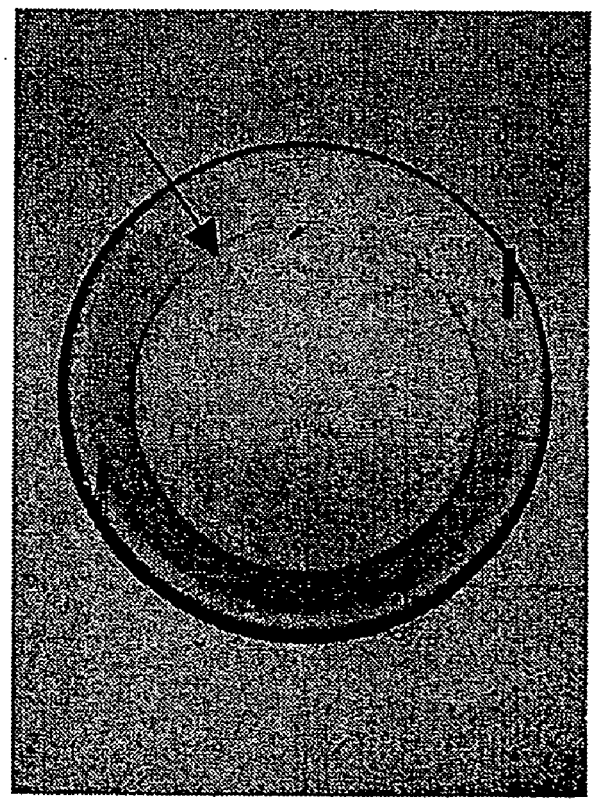
Figure 3 Micrograph of the impregnated acrylic IOL after irradiation showing an adjusted zone (indicated by arrow)

METHOD FOR MAKING NOVEL COMPOSITIONS CAPABLE OF POST FABRICATION MODIFICATION

CROSS-REFERENCE TO RELATED APPLICATIONS

This application is a continuation of U.S. Ser. No. 10/911,029, filed Aug. 3, 2004, now abandoned.

STATEMENT REGARDING FEDERALLY SPONSORED RESEARCH OR DEVELOPMENT

Not applicable.

REFERENCE TO A COMPACT DISK APPENDIX

Not applicable.

TECHNICAL FIELD

The invention relates to methods for making materials whose properties can be modified by stimulus induced polymerization of modifiers dispersed in the material. The materials can be used to make adjustable optical elements such as light adjustable intraocular lenses for the phakic or aphakic patient.

BACKGROUND OF THE INVENTION

Approximately two million cataract surgery procedures are performed in the United States annually. The procedure generally involves making an incision in the anterior lens capsule to remove the cataractous crystalline lens and implanting an intraocular lens in its place. The power of the implanted lens is selected (based upon pre-operative measurements of ocular length and corneal curvature) to enable the patient to see without additional corrective measures (e.g., glasses or contact lenses). Unfortunately, due to errors in measurement, and/or variable lens positioning and wound healing, about half of all patients undergoing this procedure will not enjoy optimal vision without correction after surgery. Brandser et al., *Acta Ophthalmol Scan* 75:162-165 (1997); Oshika et al., *J. Cataract Refract Surg* 24:509-514 (1998). Because the power of prior art intraocular lenses generally cannot be adjusted once they have been implanted, the patient typically must choose between replacing the implanted lens with another lens of a different power or be resigned to the use of additional corrective lenses such as glasses or contact lenses. Since the benefits typically do not outweigh the risks of the former, it is almost never done.

An intraocular lens whose power may be adjusted after implantation and subsequent wound healing would be an ideal solution to post-operative refractive errors associated with cataract surgery. Moreover, such a lens would have wider applications and may be used to correct more typical conditions such as myopia, hyperopia, and astigmatism. Although surgical procedures such as LASIK which uses a laser to reshape the cornea are available, only low to moderate myopia and hyperopia may be readily treated. In contrast, an intraocular lens, which would function just like glasses or contact lenses to correct for the refractive error of the natural eye, could be implanted in the eye of any patient. Because the power of the implanted lens may be adjusted, post-operative refractive errors due to measurement irregularities and/or variable lens positioning and wound healing may be fine tuned in-situ. One solution has been proposed in U.S. Pat. No. 6,450,642. In this patent, optical elements such as intraocular lenses are created having a refraction modifying composition (RMC) dispersed throughout the lens. Dispersion of the RMC throughout the lens is accomplished by forming the base lens in the presence of the RMC. The result is a lens whose optical properties can be adjusted by localized polymerization of the RMC.

While this process is effective in creating an adaptable lens, the presence of the macromer during the formation process often results in at least some of the macromers being polymerized into the matrix of the lens. This reduces the amount of macromer available for subsequent polymerization. Additionally, the polymerization reaction of the base polymer must be mutually exclusive from the polymerization of the macromer.

It is desirable, therefore, to make a material whose properties can be manipulated through the use of modifiers dispersed in the material in a manner that the modifiers are not consumed during the initial fabrication process and the base material can be polymerized by any polymerization reaction including photo-polymerization.

BRIEF SUMMARY OF THE INVENTION

The invention relates to a novel method for preparing materials whose properties can be adjusted by stimulus induced polymerization of modifiers dispersed in the base material. The present method eliminates the unintentional, incidental polymerization of the modifiers during the formation of the base material and enables the formation of the base material independent of that of the photo reactive macromer.

In the present method, a base material is preferably formed in the presence of a non-reactive spacer material forming a network structure with the spacer-material dispersed therein. The spacer material is then removed from the base material and replaced with a modifier. The displacement of the spacer-material by the modifier does not significantly affect the characteristics of the base material. The base material can also be formed without a non-reaction spacer-material provided it forms a network which will allow the subsequent introduction of macromer.

Once the modifier has been dispersed throughout the base material, the properties of the base material can be modified by exposing at least a portion of the base material to an external stimulus. This, in turn, induces polymerization of the modifier in the exposed region, which in turn causes changes in one or more properties of the base material. The properties, which can be changed include the shape of the material, optical properties such as refractive index of the material and other physical properties such as elasticity and flexibility.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1 is a plot showing increase of weight versus times from Example 1;

FIG. 2 is a photomicrograph of a lens impregnated with a modifier;

FIG. 3 is a photomicrograph of a lens of FIG. 2 post eradication.

DETAILED DESCRIPTION OF THE INVENTION

Novel materials have been developed which can be tailored for different uses by exposure of at least a portion of the material to an external stimuli such as light. The materials comprise a modifier dispersed throughout the material which, when exposed to an external stimulus, polymerizes thereby causing changes in at least one property of the material in the exposed region.

These materials are particularly useful in the area of optics where the shape and refractive index of the material in the exposed region can be altered. For example, the materials can be used to manufacture light adjustable lenses such as those described in U.S. Pat. No. 6,450,642.

The adjustable materials are generally prepared by creating the base material in the presence of the modifiers. For example, U.S. Pat. No. 6,450,642 teaches the formation of a first polymer matrix in the presence of a refraction modulating composition to form an optical element with the RMC dispersed throughout the element. While this yields a base whose properties are capable of post fabrication modification, the formation of the lens in the presence of the modifier results in some of the modifier being incorporated into the polymer matrix, leaving it unavailable for future polymerization. The formation of the first polymer matrix is also limited to methods which do not significantly alter the reactivity of the macromer.

The present method provides for the formation of the base material followed by impregnation with the modifier. The base material is formed in a manner that allows the modifier to readily diffuse into the material. This can be accomplished by forming the base material from a composition that in and of itself comprises a structure with sufficient porosity to allow the modifier to diffuse into the base material. Alternatively, the base material can be formed in the presence of a non-reactive spacer composition which can diffuse out of the base material leaving a structure that permits the modifier to diffuse into the base material. The base material is generally found in the shape required for the end use of the product. For example, when the final product is intended to be a lens, the base material is found in the shape of a lens. The same holds true for the application of the same material including, but not limited to, various optical elements, such as contact lenses, intraocular lenses, spectacle lenses, magnifying lenses, telescopic lenses, microscopic lenses, mirrors, recordable media such as compact disks or DVD disks.

Once the base material is formed, the modifier is then allowed to diffuse into the base material. The modifier becomes dispersed throughout the base material. Once the modifier has been dispersed throughout the base material, the impregnated material is then ready for use. For example, in the case of an adjustable IOL, the base material is formed in the shape of an IOL. The IOL can then be impregnated with a modifier. The lens can then be implanted in a patient using standard techniques. The properties of the IOL can then be modified by exposing at least a portion of the IOL to an external stimulus which induces polymerization of the modifier.

As discussed above, the polymerization of the modifier with the base material induces changes in the properties of the lease material. This generally occurs due to the formation of the polymer matrix by the modifier. This modifying matrix can cause changes in several ways. One change that can be induced is changes in the flexural modules of the base material. Another is a change in the refractive index. Finally, formation of the modifying matrix can cause changes in the shape of the lens.

Shape changes are accomplished by impregnation of unpolymerized modifiers from the unexposed region to the exposed region. The amount of modifiers which will migrate is time dependent and can be carefully controlled. If enough time is permitted, the modifying composition will equilibrate and redistribute throughout the implant. When the region is re-exposed to the energy source, the modifying composition that has since migrated into the region (which may be less than if the modifying composition were allowed to re-equilibrate) polymers to further increase the formation of the polymer matrix. This process (exposure followed by an appropriate time interval to allow for diffusion) may be repeated until the exposed region of the implant has reached the desired property. At this point, the entire implant is exposed to the energy source to "lock-in" the desired property by polymerizing the remaining modifying composition that are outside the exposed region before the components migrate into the exposed region.

The base material typically comprises a polymer matrix. The base matrix is a physically or covalently linked structure that functions as an implant.

In general, the base matrix is formed from one or more monomers that upon polymerization will form the first polymer matrix. The base matrix composition optionally may include any number of formulation auxiliaries that modulate the polymerization reaction or improve any property of the base material. Illustrative examples of suitable monomers include acrylates, methacrylates, phosphazenes, siloxanes, vinyls, homopolymers and copolymers thereof. As used herein, a "monomer" refers to any unit (which may itself either be a homopolymer or copolymer) which may be linked together to form a polymer containing repeating units of the same. If the monomer is a copolymer, it may be comprised of the same type of monomers (e.g., two different siloxanes) or it may be comprised of different types of monomers (e.g., a siloxane and an acrylic).

In one embodiment, the one or more monomers that form the base material are polymerized and cross-linked in the presence of a non-reactive diluent or spacing compound. In another embodiment, polymeric starting material that forms the base material is cross-linked in the absence of the non-reactive diluent or spacer compound in a manner that it forms a network which can accept the macromers. Under either scenario, the spacer compounds must be compatible with and not appreciably interfere with the formation of the base material. Similarly, the formation of the modifier matrix should also be compatible with the existing base material. For example, for an IOL, the base matrix and the modifier matrix should not phase separate and light transmission by the optical element should be unaffected.

The spacer compound should be non-reactive, i.e. it should not participate in the polymerization of the implant matrix or base material. It must be large enough to create voids or passages in the implant matrix to allow diffusion of the spacer composition out of the matrix and diffusion of the modifying composition into the matrix. Suitable spacer compounds include but is not limited to silicon alkanoates, silicone fluids and $C_1$-$C_{18}$ dioldialkarioades.

As described previously, the modifier may be a single component or multiple components so long as: (1) it is compatible with the base matrix; (2) it remains capable of stimulus-induced polymerization after impregnation of the base material in at least one embodiment. The modifier may be freely diffusible within the base material In preferred embodiments, the stimulus-induced polymerization is photo-induced polymerization.

The adjustable material of the invention have numerous applications. Most specifically, they are employed as intraocular lenses.

In general, there are two types of intraocular lenses ("IOLs"). The first type of an intraocular lens replaces the eye's natural lens. The most common reason for such a procedure is cataracts. The second type of intraocular lens supplements the existing lens and functions as a permanent corrective lens. This type of lens (sometimes referred to as a phakic intraocular lens) is implanted in the anterior or posterior chamber to correct any refractive errors of the eye. In theory, the power for either type of intraocular lenses required for emmetropia (i.e., perfect focus on the retina from light at infinity) or desired visual outcome of individual patients can be precisely calculated. However, in practice, due to errors in measurement of corneal curvature, and/or variable lens positioning and wound healing, it is estimated that only about half of all patients undergoing IOL implantation will enjoy the best possible vision without the need for additional correction after surgery. Because prior art IOLs are generally incapable of post-surgical power modification, the remaining patients must resort to other types of vision correction such as external lenses (e.g., glasses or contact lenses) or cornea surgery. The need for these types of additional corrective measures is obviated with the use of the intraocular lenses of the present invention.

In addition to its use as an adjustable intraocular lens, the materials described herein can be used in a number of applications where it is desirable to adjust the properties of material after it has been formed into a specific product. For example, the material can be used to fabricate a wide array of optical elements or material such as spectacle lenses, mirrors, contact lenses, telescopic lenses, recordable media, such as compact disks, and the like. The material can also be used to form various types of implants where it may be desirable to modify the shape or physical properties of the implant after it has been implanted.

Illustrative examples of a base material include: poly-acrylates such as poly-alkyl acrylates and poly-hydroxyalkyl acrylates; poly-methacrylates such as poly-methyl methacrylate ("PMMA"), poly-hydroxyethyl methacrylate ("PHEMA"), and poly-hydroxypropyl methacrylate ("HPMA"); poly-vinyls such as poly-styrene and poly-vinylpyrrolidone ("PNVP"); poly-siloxanes such as poly-dimethylsiloxane; poly-phosphazenes, and copolymers of thereof. U.S. Pat. No. 4,260,725 and patents and references cited therein (which are all incorporated herein by reference) provide more specific examples of suitable polymers that may be used to form the first polymer matrix.

In preferred embodiments, the base material generally possesses a relatively low glass transition temperature ("$T_g$") such that when used to make an IOL, the IOL tends to exhibit fluid-like and/or elastomeric behavior, and is typically formed by crosslinking one or more polymeric starting materials wherein each polymeric starting material includes at least one crosslinkable group. Illustrative examples of suitable crosslinkable groups include but are not limited to hydride, acetoxy, alkoxy, amino, anhydride, aryloxy, carboxy, enoxy, epoxy, halide, isocyano, olefinic, and oxime. In more preferred embodiments, each polymeric starting material includes terminal monomers (also referred to as endcaps) that are either the same or different from the one or more monomers that comprise the polymeric starting material but include at least one crosslinkable group. In other words, the terminal monomers begin and end the polymeric starting material and include at least one crosslinkable group as part of its structure.

Modifier is as described above except that it has the additional requirement of biocompatibility. The refraction modulating composition is capable of stimulus-induced polymerization and may be a single component or multiple components so long as: (1) it is compatible with the base material; (2) is capable of stimulus-induced polymerization within the base material. In one embodiment, the modifier is also freely diffusible within the base material. In general, the same type of monomers that is used to form the base material may be used as a component of the modifier. However, where it is desirable for the modifier to be diffusible within the base material, the modifier monomers generally tend to be smaller (i.e. have lower molecular weights) than the polymers which form the base material. In addition to the one or more monomers, the modifier composition may include other components such as initiators and sensitizers that facilitate the formation of the second polymer matrix.

In preferred embodiments, the stimulus-induced polymerization is photo-polymerization. In other words, the one or more monomers that comprise the refraction modulating composition each preferably includes at least one group that is capable of photo-polymerization. Illustrative examples of such photo-polymerizable groups include but are not limited to acrylate, allyloxy, cinnamoyl, methacrylate, stibenyl, and vinyl. In more preferred embodiments, the refraction modulating composition includes a photoinitiator (any compound used to generate free radicals) either alone or in the presence of a sensitizer. Examples of suitable photoinitiators include acetophenones (e.g.,—substituted haloacetophenones, and diethoxyacetophenone); 2,4-dichloromethyl-1,3,5-triazines; benzoin ethers; and o-benzoyl oximino ketone. Examples of suitable sensitizers include p-(dialkylamino)aryl aldehyde; N-alkylindolylidene; and bis[p-(dialkylamino)benzylidene] ketone.

Where flexibility is important, such as in the case of an IOL, one class of modifiers that can be used is poly-siloxanes endcapped with a terminal siloxane moiety that includes a photo-polymerizable group. An illustrative representation of such a monomer is

wherein Y is a siloxane which may be a monomer, a homopolymer or a copolymer formed from any number of siloxane units, and X and $X^1$ may be the same or different and are each independently a terminal siloxane moiety that includes a photo-polymerizable group. An illustrative example of Y include

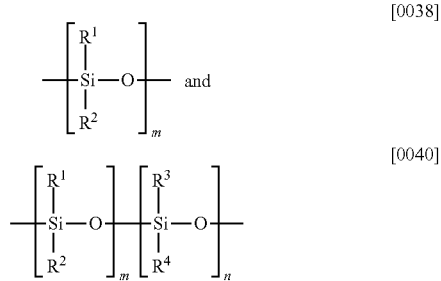

[0038]

[0040]

wherein: m and n are independently each an integer and $R^1$, $R^2$, $R^3$, and $R^4$ are independently each hydrogen, alkyl (primary, secondary, teritary, cyclo), aryl, or heteroaryl. In preferred embodiments, $R^1$, $R^2$, $R^3$, and $R^4$ are a $C_1$-$C_{10}$ alkyl or phenyl. Because modifiers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, and $R^3$ are the same and are methyl, ethyl or propy and $R^4$ is phenyl.

Illustrative examples of X and $X^1$ (or $X^1$ and X depending on how the modifier is depicted) are

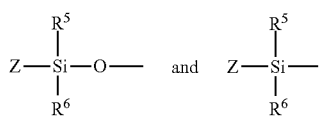

respectively wherein: $R^5$ and $R^6$ are independently each hydrogen, alkyl, aryl, or heteroaryl; and Z is a photo-polymerizable group.

In preferred embodiments, $R^5$ and $R^6$ are independently each a $C_1$-$C_{10}$ alkyl or phenyl and Z is a photo-polymerizable group that includes a moiety selected from the group consisting of acrylate, allyloxy, cinnamoyl, methacrylate, stibenyl, and vinyl. In more preferred embodiments, $R^5$ and $R^6$ is methyl, ethyl, or propyl and Z is a photo-polymerizable group that includes an acrylate or methacrylate moiety.

In one embodiment, a modifier is of the following formula

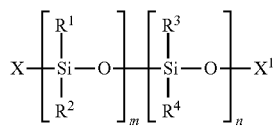

wherein X and $X^1$ and $R^1$, $R^2$, $R^3$, and $R^4$ are as defined previously. Illustrative examples of such modifiers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group. Although any suitable method may be used, a ring-opening reaction of one or more cyclic siloxanes in the presence of triflic acid has been found to be a particularly efficient method of making one class of inventive modifiers. Briefly, the method comprises contacting a cyclic siloxane with a compound of the formula

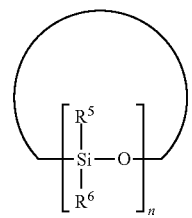

in the presence of acid or base catalysts wherein $R^5$ and $R^6$ are independently each hydrogen, alkyl, aryl, or heteroaryl. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethylsiloxane methyl-phenylsiloxane copolymer that is endcapped with a methacryloxylpropyl-dimethylsilane group, an especially preferred modifier.

Another class of modifiers useful in the practice of the invention are acrylate based modifiers having the general formula

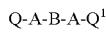

Q-A-B-A-$Q^1$ whereby A is

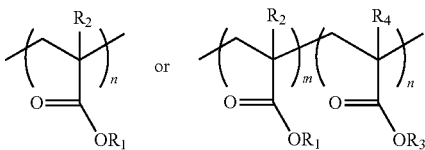

wherein m and n are integers, and $R_1$, $R_2$, $R_3$, and $R_4$ are independently selected from a group comprising of alkyl, halogenated alkyl, phenyl, hydrogen, and aryl moieties.

B is a dihalide-containing acrylate initiator. Q and $Q^1$ are photopolymerizable groups including acrylate, allyloxy, cinnamoyl, methacrylate, and vinyl with acrylate and methacrylate being preferred.

The modifier will have the general chemical structure:

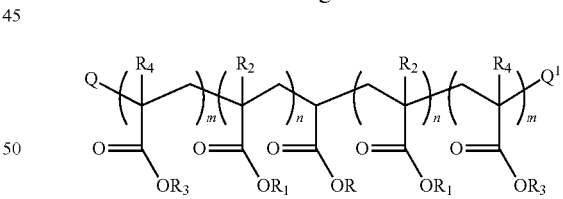

wherein m and n are integers, and R, $R_1$, $R_2$, $R_3$, and $R_4$, are independently selected from the group consisting of alkyl, halogenated alkyl, aryl, and hydrogen.

The molecular weights of the modifier will range from 500 to 400 with 1000 g/mol preferred. The modifier will have a polydispersity index (PDI) of from 1.0 to about 2.0 with a PDI of 1.0 preferred.

The method of the present invention permits the formation of materials whose properties can be adjusted after the fabrication of an object. In the method, a lens material is formed in a manner that creates a matrix into which modifiers can be introduced. Thus the matrix must have spacers in voids large enough to permit the introduction of modifiers after the lens material is formed. The voids or spaces are then at least partially filled with a modifier that is capable of inducing changes into the lens material when the modifier is exposed to an external stimulus such as heat or light.

In one embodiment, the method comprises:

Forming a base material in the presence of a spacer material;

Impregnating the base material with a modifier such that the modifier displaces at least a portion of the spacer material. This results in a base material that has the modifiers dispersed throughout at least a portion of the base material.

The base material can be formed in any manner known to those skilled in the art. Typically, it is formed by the polymerization of monomers such as those described above. The mechanism for polymerization can be the same or different from that used to polymerize the modifiers subsequent to their introduction into the base material. Thus, in the practice of the present invention, it is possible to form the base material through photo-polymerization and still employ modifiers that are also photo-polymerizable.

As discussed above, once the base material is formed, at least a portion of the spacer material is replaced with the modifier. This can be accomplished during the diffusion process where the modifier displaces the spacer compound as the modifier diffuses into the base material. Alternatively, at least a portion of the spacer material can be removed from the base material before the introduction of the modifier.

The spacer-material can be removed by any means known to the art that does not destroy the integrity of the base material and/or prevent the subsequent introduction of modifier. Among the methods which can be used are evaporation and solvent extraction. Once at least a portion of the spacer compound has been removed, the base material is then impregnated with the modifier. This is typically accomplished by immersing the base material in a bath comprising the modifiers and any initiator required to induce polymerization of the modifier. Other methods for introducing the modifier into the base material which are well known to those skilled in the art may also be used.

The introduction of the modifier does generally not affect the physical properties of the base material. For example, the introduction of a modifier into a lens made from a base material, generally does not affect the optical properties (such as transparency or clarity) of the lens. However, modifiers having a different refraction index from the base material may be used as long as they are compatible with the base material. Only the subsequent polymerization of, at least a portion of the modifier present, induces changes in the refractive power of the base material. The change in properties also occurs without the need for further processing such as the removal of unreacted modifiers. This permits the materials of the invention to be created, set in place, and modified in place without the need to modify the material before it is placed or to remove the material for modification. This is particularly useful for implants such as IOLs when the properties can be modified after the lens has been implanted in the patient. Another application for the materials of the invention is in remotely located telescopes and the like. Through use of these materials, flaws or aberrations which may appear in the lenses or moreover used in these devices can be corrected or compensated for by modifying the elements in place. Other applications of these materials will be readily apparent to those skilled in the art.

As noted above, the base material is usually formed in the general shape needed for the ultimate application. For example, when the base material is to be used to create an adjustable intraocular lens, the lens material is formed in the shape of an IOL. This is usually accomplished by polymerizing the monomers that form the base material in a mold. Other methods for forming and shaping the base material well known to those skilled in the art may be employed in the practice of the invention.

One of the principle uses of the present invention is the formation of adjustable intraocular lenses particularly when the base lens and the modifiers are both polymerized using similar mechanisms, e.g. where both are to be photopolymerized. The method allows the function of the base lens without incidental polymerization of the modifier.

In practice, the components of the base material are combined in a mold and polymerized to form a base material in the shape of the desired end product. A spacer compound is also present to ensure the creation of a matrix with sufficient spaces or voids to allow the modifier to become dispersed throughout the base material.

Once the base material is formed, the material is moved from the mold. In some applications, at least a portion of the spacer compound is removed. The removal of the spacer material may cause a change in the shape of the base material. The introduction of the modifier will usually restore the lens to its original shape. This is opposed to the swelling that is observed in the prior unit when polymerizable materials are introduced into an optical matrix. In the present invention significant changes in shape only occur when there is migration of modifier between regions of the base polymer following polymerization of the modifier and the base material has sufficient elasticity to permit the change in shape.

Once the base material has been impregnated with the modifier, the base material is then ready to be put into place. Again referring to intraocular lenses, this means that the lens is ready for implantation. This is accomplished using well known surgical techniques.

After implanting the lens, and allowing sufficient time for wound healing, the patient is then evaluated for visual acuity. If the patient's vision is within acceptable limits, the entire lens is then exposed to an external stimulus, to polymerize all of the available modifiers. If the patient's vision is not within the desired limits, a portion or portions of the lens is exposed to an external stimulus which in turn induces polymerization of the modifier in the exposed regions. This causes changes in the optical properties of the lens such as the refractive index of the base material, the curvature of the lenses or both. In this manner, the lens can be altered to provide the patient the desired visual acuity. The process can be repeated until the desired visual acuity is achieved. Once this occurs, the entire lens is then exposed to the stimulus to "lock-in" the desired properties in the manner described above.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

EXAMPLES

Example 1

An acrylic based IOL was impregnated with a modifying composition comprising a mixture of a photoinitiator and hexandioldimethacrylate. In this example, the lens was immersed in the mixture for 16 hours. This ensured sufficient time to permit the acrylic modifiers to diff-use throughout the lens. FIG. 1 shows a plot of increase in weight vs time for these lenses. A loading of 135 wt % of the modifier was achieved over a period of 16 hours. This demonstrates the ability of the acrylic lens to absorb a modifier after fabrication.

Example 2

In this example, an acrylic IOL was impregnated with approximately 30 wt % of the modifiers and in the manner described in example 1. FIG. 2 is a micrographic of the lens after impregnation. The lens was then exposed to UV light at 365 nm for two minutes using a pre-set pattern. FIG. 3 is a micrograph of the lens post irradiation. As seen in FIG. 3, an adjustment zone has been created in the center of the lens.

Example 3

Acrylic lenses were molded from a mixture of n-butyl acrylate, trifluoroethyl methacrylate, glycidyl methacrylate, photoinitiator, and hexanediol diisobutyrate as unreactive diluent. This base molding material was prepolymerized by irradiation with UV light to form a prepolymer of a suitable viscosity for lens molding. Lenses were then molded by photopolymerization with UV light. After photopolymerization and post-cure at 50° C., the lenses were extracted with methanol to remove nonfunctional spacer material. Following extraction with methanol, the lenses were impregnated with an acrylic oligomer endcapped with methacrylate groups. Treatment at 50° C. for equilibration and relaxing of the lens structure gave optically clear lenses. These lenses were subsequently irradiated with patterned UV light to create a refraction change of the lens. FIG. 4 shows interferograms of these lenses before and after irradiation.

What is claimed is:

1. A method for making an adjustable material comprising forming an acrylate derived base material in the presence of a spacer material;
   displacing at least a portion of the spacer material by impregnating the base material with a silicon derived and/or acrylate derived photopolymerizable modifier, upon stimulus induced photopolymerization of said modifier, the refractive power of the adjustable material is changed by adjusting the refractive index, shape or both.

2. The method of claim 1 wherein the stimulus is light.

3. The method of claim 2 wherein the light is UV light.

4. The method of claim 1 wherein the base material is formed in the shape of an optical element.

5. The method of claim 1 wherein the base material is a co-polymer further comprising at least one polymer selected from the group consisting of polyacrylate, poly-methacrylate, polyvinyl, polysiloxane and poly-phosphazene.

6. The method of claim 1 wherein the spacer material is selected from the group consisting of silicon alkanoates, silicon fluids, acrylic dialkanoates and $C_1$ to $C_{18}$ dioldialkanoates.

7. The method of claim 1 wherein the modifier has the general formula $$X—Y—X^1$$

wherein Y is a siloxane group having the general formula suited from

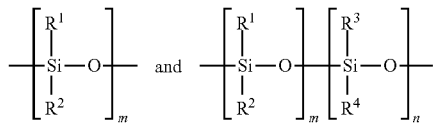

wherein m and n are integers and $R^1$, $R^2$, $R^3$ and $R^4$ are independently selected from the group consisting of hydrogen, alkyl, aryl, and heteroaryl and X has the general formula

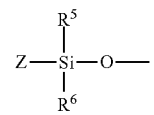

and $X^1$ has the general structure

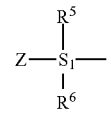

wherein $R^5$ and $R^6$ are independently selected from the group consisting of hydrogen, alkyl, aryl or heteroaryl and Z is a photopolymerizable group.

8. The method of claim 1 wherein the modifier is an acrylate based modifier having the general formula $$Q\text{-}A\text{-}B\text{-}A\text{-}Q^1$$

wherein A has the general formula selected from

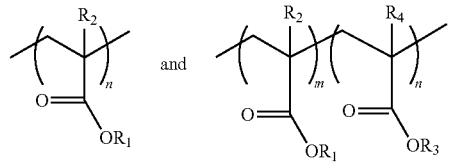

and
   wherein m and n are integers and $R_1$, $R_2$, $R_3$ and $R_4$ are independently selected from the group consisting of alkyls, halogenated alkyls, phenyl, hydrogen and aryl; B is a dihalide containing acrylate initiator and Q and $Q^1$ are photopolymerizable groups.

9. The method of claim 1 where the modifier has the general formula:

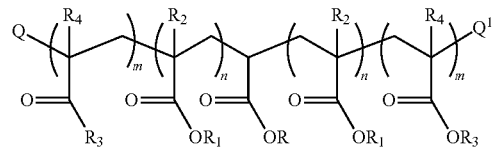

wherein R, $R_1$, $R_2$, $R_3$ and $R_4$ are independently selected from the group consisting of alkyls, halogenated alkyls, aryls and hydrogen, m and n are integers and Q and $Q^1$ are photopolymerizable groups.

10. A method for making an adjustable material comprising:
   forming a base material in the presence of a spacer material;
   displacing at least a portion of the spacer material by impregnating the base material with a silicon derived and/or acrylate derived photopolymerizable modifier,
   upon stimulus induced photopolymerization of said modifier, the refractive power of the adjustable material is changed by adjusting the refractive index, or shape or both after the material has been formed into a specific product,
   wherein the specific product is selected from the group consisting of spectacle lenses, mirrors, contact lenses, telescopic lenses, recordable media, and intraocular lenses.

11. A method for making an adjustable material comprising
   forming a base material in the presence of a spacer material thereby creating a polymer matrix with voids;
   removing the spacer material from the polymer matrix of the base material, wherein upon removal of the spacer material the polymer matrix retains its shape;
   impregnating the base material with a silicon derived and/or acrylate derived photopolymerizable modifier, said modifier does not cause the base material to change shape or swell; and,
   wherein upon stimulus induced photopolymerization of said modifier, the refractive power of the adjustable material is changed by adjusting the refractive index, shape or both.

* * * * *